United States Patent
Hara et al.

(10) Patent No.: US 8,673,577 B2
(45) Date of Patent: Mar. 18, 2014

(54) METHOD FOR EXAMINING ACUTE RENAL DISORDER

(75) Inventors: Masanori Hara, Niigata (JP); Hiroyuki Kurosawa, Gosen (JP); Shinya Ogasawara, Gosen (JP); Yoshiaki Hirayama, Gosen (JP)

(73) Assignees: Masanori Hara, Niigata (JP); Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 13/579,906

(22) PCT Filed: Feb. 24, 2011

(86) PCT No.: PCT/JP2011/054106
§ 371 (c)(1), (2), (4) Date: Aug. 17, 2012

(87) PCT Pub. No.: WO2011/105474
PCT Pub. Date: Sep. 1, 2011

(65) Prior Publication Data
US 2012/0322087 A1 Dec. 20, 2012

(30) Foreign Application Priority Data
Feb. 26, 2010 (JP) .................................. 2010-041748

(51) Int. Cl.
*G01N 33/53* (2006.01)
(52) U.S. Cl.
USPC .......................................... 435/7.1; 436/518
(58) Field of Classification Search
None
See application file for complete search history.

(56) References Cited

FOREIGN PATENT DOCUMENTS

| EP | 1 336 845 A1 | 8/2003 |
| WO | WO02/37099 | 5/2002 |
| WO | WO2010/143422 | 12/2010 |

OTHER PUBLICATIONS

Achenbach et al. (Nephrol. Dial. Transplant 2008 vol. 23, p. 3138-3145).*
Hara et al., Nephron, 1995, vol. 69, pp. 397-403.
Masanori Hara, Kidney and dialysis, Oct. 25, 2008, vol. 65 (No. 4), pp. 488-491.
Shigeru Seikine and Masanori Hara, Ther. Res., 2008, vol. 29 (No. 11), pp. 1900-1904.
Solez et al., "Podcyte Change in Early Acute Renal Failure (ARF)," Kidney International, 1981, vol. 19, No. 1, p. 214.
M. Hara et al.: "Inmunohistochemical and urinary markers of podocyte injury," Pediatric Nephrology, 1998, vol. 12, pp. 43-48.
H. Hara et al.: "Apical Cell Membranes Are Shed into Urine from Injured Podocytes: A Novel Phenomenon of Podocyte Injury," Journal of the American Society of Nephrology, Jan. 12, 2005, vol. 16, No. 2, pp. 408-416.

* cited by examiner

*Primary Examiner* — Jacob Cheu
(74) *Attorney, Agent, or Firm* — Don D. Cha; Hamilton DeSanctis & Cha, LLP

(57) ABSTRACT

Provided is a test method for acute kidney injury, including detecting urinary podocalyxin. According to the test method, a subject to be tested who has a higher value for the urinary podocalyxin than a reference value can be assessed to have acute kidney injury. Further, as compared to a conventional method, the test method allows acute kidney injury to be assessed accurately and non-invasively, which allows a physical burden on a patient to be reduced. Thus, the test method is useful.

8 Claims, 2 Drawing Sheets

METHOD FOR EXAMINING ACUTE RENAL DISORDER

TECHNICAL FIELD

The present invention relates to a test method for acute kidney injury, including detecting urinary podocalyxin, and to a test reagent for acute kidney injury for use in the test method, including an anti-podocalyxin antibody.

The present application claims priority from Japanese Patent Application No. 2010-041748, which is incorporated herein by reference.

BACKGROUND ART

In recent years, emphasis in acute renal failure (ARF) has been put not only on a structural abnormality, i.e., acute tubular necrosis, but also on a functional abnormality in renal hemodynamics. In diagnosis and therapy as well, a concept of ARF has been gradually replaced by that of acute kidney injury (AKI), and importance of early diagnosis and therapy has been advocated.

The acute kidney injury refers to a state in which renal function has rapidly deteriorated and the acute kidney injury is characterized by deterioration of renal function by tubular necrosis in many cases. Causes of the acute kidney injury include prerenal renal failure, intrinsic renal failure, and postrenal renal failure. The prerenal renal failure is caused when the kidneys are subjected to ischemia owing to a decrease in extracellular fluid volume through traumatic bleeding, dehydration, emesis, diarrhea, or the like, a reduction in effective circulating blood volume through cardiogenic shock or the like, and a decrease in renal blood flow through dissecting aortic aneurysm, renal artery thrombosis, or the like. The intrinsic renal failure involves direct injury caused in a renal tissue, such as glomerular injury (acute glomerulonephritis, rapidly progressive glomerulonephritis, polyarteritis nodosa, or the like), acute tubular necrosis (due to an antibiotic such as an aminoglycoside-based antibiotic, an anti-inflammatory analgesic, an antitumor drug, a contrast agent, or the like), or acute interstitial nephritis (due to an antibiotic such as a β-lactam-based antibiotic, an anti-inflammatory analgesic, an anticonvulsive drug, or the like). The postrenal renal failure involves urinary excretion disorder caused by occurrence of obstruction in the middle of a passage of urine, such as ureteral obstruction (ureteral calculi), bladder obstruction or urethral obstruction (prostatic hyperplasia, prostate cancer), or pelvic tumor.

The acute kidney injury includes many diseases that require ICU management because the diseases occur, for example, after open-heart surgery and aorta replacement. Hence the condition of the acute kidney injury needs to be grasped on an hourly basis after its development. Currently, no improvement in life prognosis of the acute kidney injury can be expected without early diagnosis and early therapeutic intervention.

Conventionally, diagnosis for the acute kidney injury has been performed based on serum creatinine and a urinary amount in ordinary cases. However, the diagnosis based on those two items has had a problem. No established diagnostic standards have existed for those two items, and 35 types of definitions of the acute kidney injury have existed. As a global approach to solving this problem, the Acute Kidney Injury Network has been established and proposed a diagnostic standard for the acute kidney injury. The diagnostic standard specifies that a diagnosis of acute kidney injury is made when the following conditions are satisfied: (1) serum creatinine increases by 1.5 times or more or by 0.3 mg/dL or more; and (2) oliguria at 0.5 mL/kg per hour continues 6 hours or more. Further, like a stage classification of chronic kidney disease, stage classifications of the acute kidney injury (RIFLE classification, AKIN classification, and the like) have been particularly proposed.

However, the diagnosis based on the two items still has a problem. Serum creatinine does not immediately increase even when a glomerular filtration rate decreases in association with kidney injury. However, serum creatinine may continue to increase for some time even when the glomerular filtration rate shows a tendency toward recovery. Accordingly, it cannot be said that serum creatinine is highly useful as each of an early marker for detecting an acute change and a marker for monitoring a therapeutic effect and predicting prognosis. In addition, serum creatinine is easily influenced by non-renal factors such as body weight, race, sex, drugs, muscle metabolism, and trophic condition. Further, the diagnosis based on a urinary amount requires a long period of time and hence the urinary amount is not suitable as a marker for the acute kidney injury, the condition of which needs to be grasped on an hourly basis after its development. Therefore, there is urgent need for development of a biomarker which allows easy measurement, is hardly influenced by other biological factors, and enables early detection, risk classification, and prognostic prediction of the disease.

As a substance found in association with a renal disease, there is known urinary podocalyxin, and there is disclosed a simple test measure for kidney injury involving measuring urinary podocalyxin (Patent Literature 1). Podocalyxin is a glycoprotein which is present in surfaces of podocytes constructing the renal glomerulus and is responsible for a filtration function. The podocytes are located on the Bowman's space side in the glomerular basement membrane and play important roles in the mechanism of glomerular filtration. Thus, it is known that the grasping of the degree of injury in the podocytes has an extremely important meaning in understanding a renal disease (Non Patent Literature 1). It is known that, in usual cases, urinary podocytes do not appear in non-glomerular renal disease and non-inflammatory glomerular renal disease, but do appear in inflammatory glomerular renal disease. Particularly in a case with robust findings in acute glomerular inflammation, a large number of podocytes appear (Non Patent Literatures 2 and 3). However, there is still no report on what behaviors the podocytes and podocalyxin show in the acute kidney injury resulting from various causes.

CITATION LIST

Patent Literature

[PTL 1] WO 2002/037099 A1

Non Patent Literature

[NPL 1] Hara et al., Nephron 69: 397-403 (1995)
[NPL 2] Masanori Hara, Novel tests useful for medical care of renal disease, urinary podocyte test and quantitation of urinary podocalyxin, Kidney and Dialysis, Oct. 25, 2008, Vol. 65 No. 4
[NPL 3] Sakari Sekine, Masanori Hara, Novel markers for kidney injury—Urinary podocytes and podocalyxin and their clinical significance—, Ther. Res., 2008, Vol. 29 No. 11, p. 1900-1904

SUMMARY OF INVENTION

Technical Problem

An object of the present invention is to provide a test method for acute kidney injury.

Solution to Problem

In order to achieve the object, the inventors of the present invention have focused attention on the fact that a patient with acute kidney injury has a higher urinary podocalyxin concentration than a healthy subject, and have found that a test for acute kidney injury can be performed through the detection of urinary podocalyxin. Thus, the present invention has been completed.

That is, the present invention includes the following items.
1. A test method for acute kidney injury, including detecting urinary podocalyxin.
2. A test method according to the above-mentioned item 1, further including assessing a subject to be tested who has a higher value for the urinary podocalyxin than a reference value to have acute kidney injury.
3. A test method according to the above-mentioned item 3, in which the reference value includes a value for an upper limit of a 95% confidence interval of a value for urinary podocalyxin in a healthy subject.
4. A test method according to any one of the above-mentioned items 1 to 3, in which the value for the urinary podocalyxin includes a value corrected with a value for a urinary component.
5. A test method according to the above-mentioned item 4, in which the urinary component includes urinary creatinine.
6. A test method according to any one of the above-mentioned items 1 to 5, in which the acute kidney injury includes acute kidney injury due to acute tubular injury.
7. A test method according to any one of the above-mentioned items 1 to 6, in which the detecting of the urinary podocalyxin is performed by an immunological technique.
8. A test reagent for acute kidney injury for use in the test method of the above-mentioned item 7, including an anti-podocalyxin antibody for detecting urinary podocalyxin.
9. A test reagent kit for acute kidney injury for use in the test method of the above-mentioned item 7, including a reagent for detecting urinary podocalyxin using an anti-podocalyxin antibody.

Advantageous Effects of Invention

According to the test method of the present invention, the assessment of acute kidney injury can be performed more accurately than by a conventional test method, and time-course measurement of urinary podocalyxin can be performed to grasp the therapeutic course, severity, and prognostic evaluation of a subject to be tested (hereinafter, sometimes referred to as subject). In addition, a test for acute kidney injury can be performed non-invasively, which allows a physical burden on a subject to be reduced, and it is possible to make a rapid decision on a therapeutic strategy or the like.

DESCRIPTION OF EMBODIMENTS

Figure 1:
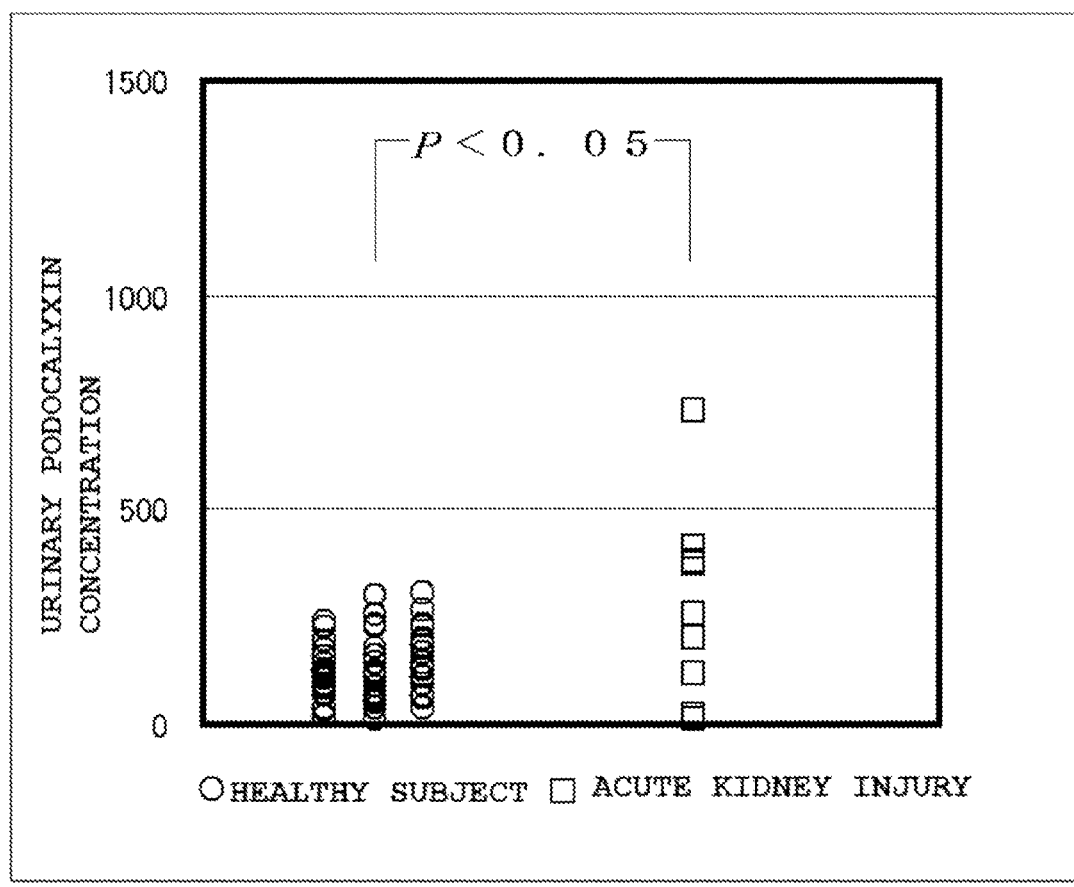
[FIG. 1] A graph showing a comparison of urinary podocalyxin concentrations between healthy subjects and patients with acute kidney injury (Example 2).

The present invention is characterized in that a test for acute kidney injury is performed through the detection of urinary podocalyxin in a subject.

Herein, urine as a specimen may be derived from any subject. No particular limitation is imposed on a collection method for urine, but it is preferred to use early morning urine or casual urine. Further, the amount of urine necessary for the test method of the present invention is about 10 to 200 µL. The test method of the present invention may be performed concurrently with a conventional general urine test.

Urine as a specimen may be treated by adding and mixing a treatment liquid into the collected urine. The treatment liquid may be any as long as the pH adjustment of the urine, the masking of a urine sediment, and the solubilization of podocalyxin are possible, but is preferably exemplified by a solution obtained by adding a chelating agent, a surfactant, and the like to a buffer. The buffer and the chelating agent may be any known buffer and chelating agent, and it is preferred to use a nonionic surfactant as the surfactant. The treatment liquid is exemplified by a solution including 0.2 M EDTA and 2% (Vol./Vol.) Triton X-100 in 2 M TES-NaOH (pH 7.0). A urine sample solution may be obtained by adding and mixing 10 µL of such treatment liquid into 90 µL of a urine specimen.

Various methods may be employed as a detection method for urinary podocalyxin in the urine sample solution. An example of the detection method for urinary podocalyxin is an immunological technique. The immunological technique may be performed, for example, by an immunostaining method (including a fluorescent antibody method, an enzymatic antibody method, a heavy metal-labeled antibody method, and a radioisotope-labeled antibody method), a combination of separation based on an electrophoresis method and a detection method with fluorescence, an enzyme, a radioisotope, or the like (including a western blot method and a fluorescent two-dimensional electrophoresis method), enzyme-linked immunosorbent assay (ELISA), a dot blotting method, latex agglutination-turbidimetric immunoassay (LA), or immunochromatography. Of those, it is preferred to employ an ELISA method or an LA method. It is preferred to employ a sandwich method among ELISA methods from the viewpoint of quantitative property. In the sandwich method, a urine sample solution is added to an anti-podocalyxin antibody-coated microtiter plate to cause an antigen-antibody reaction, an enzyme-labeled anti-podocalyxin antibody is further added to cause an antigen-antibody reaction, the plate is washed and then subjected to a reaction with an enzyme substrate and color development, the absorbance is measured to detect urinary podocalyxin, and the measured value can be used to calculate a urinary podocalyxin concentration.

The anti-podocalyxin antibody for use in the immunological technique has only to be an antibody capable of detecting podocalyxin. The anti-podocalyxin antibody for use in the present invention is not particularly limited, and may be a known antibody or an antibody to be developed in the future. Examples thereof include monoclonal and polyclonal antibodies, a labeled antibody, a chimeric antibody, a humanized antibody, and binding active fragments thereof. Further, two or more kinds of anti-podocalyxin antibodies may be used, and in that case, antibodies recognizing epitopes different from each other are preferably used.

In the present invention, a value for urinary podocalyxin may be a urinary podocalyxin concentration itself, or may be a parameter obtained by correcting the urinary podocalyxin concentration with a value concerning a urinary component to be stably excreted in urine (value for urinary component). The urinary component is particularly preferably urinary creatinine. The urinary podocalyxin concentration is preferably corrected with a urinary creatinine concentration. It is considered that the urinary creatinine concentration is substantially constant irrespective of a disease in one individual because the production of creatinine depends on the amount of a muscle. In a test for a urinary component, in order to eliminate an error in urinary amount, a technique involving correcting the amount of a urinary component of interest with an amount per g of creatinine is generally employed. This allows the comparison of the urinary component per unit gram of creatinine. A parameter obtained by correcting a urinary podocalyxin concentration with a urinary creatinine concentration is referred to as urinary podocalyxin excretion rate (PCX/Cre), which can be calculated with the following equation.

PCX/Cre: Urinary podocalyxin excretion rate (μg/g)
=100×urinary podocalyxin concentration (ng/mL)÷urinary creatinine concentration (mg/dL)       <Equation>

A subject who has a urinary podocalyxin concentration and/or a urinary podocalyxin excretion rate (PCX/Cre) which are/is obtained by the test method of the present invention and higher than a reference value(s) can be assessed to have acute kidney injury. In addition, time-course measurement and monitoring of the urinary podocalyxin concentration and/or the urinary podocalyxin excretion rate allows the therapeutic course and severity of a subject to be grasped, to thereby make a prognostic evaluation. The reference value in the present invention may be appropriately set, and a value for urinary podocalyxin in a healthy subject may be used. The healthy subject is desirably a subject who has been found to be negative for another renal function marker. The another renal function marker is exemplified by an estimated glomerular filtration rate (eGFR) and a urine protein. It is more preferred that urinary podocalyxin be detected in a plurality of healthy subjects and a value for the upper limit of the 95% confidence interval of the resultant values for urinary podocalyxin be used as a reference value. The 95% confidence interval may be determined by a known technique and can be determined with the following equation when the measured values of the healthy subjects are normally distributed.

95% Confidence interval=mean of values for urinary podocalyxin in healthy subjects±$t$×standard deviation of values for urinary podocalyxin in healthy subjects It should be noted that t represents a degree of freedom and varies depending on the number of specimens of healthy subjects, and hence is recommended to be selected based on t-distribution table. In general, t is 1.96 in the case of a 95% confidence interval.

On the other hand, when the values for urinary podocalyxin in the healthy subjects are not normally distributed, a range accounting for 95% and including the median is adopted as a reference range and a value for the upper limit thereof is adopted as a reference value for a value for urinary podocalyxin.

In the present invention, the concept of acute kidney injury (AKI) puts emphasis on not only a structural abnormality, i.e., acute tubular necrosis, but also on a functional abnormality in renal hemodynamics. Acute kidney injury refers to a state in which renal function has rapidly deteriorated, and more particularly, is characterized by deterioration of renal function by tubular injury such as tubular necrosis (in particular, acute tubular injury). The tubules are numerous tubes connecting the glomerulus to the renal pelvis. A tube located near the glomerulus is called the proximal tubule, and a tube that follows Henle's loop is called the distal tubule. Blood is filtered in the glomerulus into primary urine, which flows into the tubules. The tubules are organs for reabsorbing a substance that a living body needs from the primary urine as necessary.

Further, the concept of acute kidney injury (AKI) is distinguished from that of chronic kidney disease (CKD). Acute kidney injury and chronic kidney disease differ from each other in (a) rate of deterioration of renal function, (b) cause, (c) reversibility, and (d) therapeutic purpose. Specifically, in the case of acute kidney injury, (a) renal function deteriorates in several hours to several weeks, (b) causes include dehydration, a drug, and surgery, (c) recovery of renal function may be expected, and hence (d) the therapeutic purpose is to recover renal function. On the other hand, in the case of chronic kidney disease, (a) such a pathological condition that renal function gradually deteriorates over several months to more than ten years is exhibited, (b) causes include chronic glomerulonephritis including diabetic nephropathy and IgA nephropathy, (c) the disease is irreversible and progressive, and hence (d) the therapeutic purpose is to prevent further deterioration of renal function.

The present invention also encompasses a test reagent for acute kidney injury for use in performing a test for acute kidney injury, including an anti-podocalyxin antibody for detecting urinary podocalyxin, and a test reagent kit for acute kidney injury including the reagent. The kit may further include an instrument for collecting a specimen, a reagent such as a specimen treatment liquid or a chromogenic substrate, an instrument necessary for a test, and the like.

EXAMPLES

Hereinafter, the present invention is more specifically described by way of examples of the present invention. However, the present invention is by no means limited thereto, and various applications are possible without departing from the technical idea of the present invention.

Example 1

Measurement of Urinary Podocalyxin Concentration

A podocalyxin concentration was measured using two kinds of anti-human podocalyxin monoclonal antibodies. Those two kinds of antibodies recognize two different epitopes of human podocalyxin, respectively, and are an anti-human podocalyxin monoclonal antibody 1 (hereinafter, simply referred to as "antibody 1") and an anti-human podocalyxin monoclonal antibody 2 (hereinafter, simply referred to as "antibody 2"), respectively. In this example, an antibody 1-coated microtiter plate (split type micro plate GF8 high: Nunc) and a horseradish peroxidase (hereinafter, abbreviated as "HRP") -labeled antibody 2 were used.

First, 90 μL of urine obtained from a subject were mixed with 10 μL of a solution of 2 M TES-NaOH, 0.2 M EDTA, and 2% (Vol./Vol.) Triton X-100, pH 7.0. 100 μL of a urine sample solution obtained by the mixing were added to wells of an antibody 1-coated microtiter plate. The plate was left to stand still at 37° C. for 1 hour, and the urine sample solution was then removed by decantation from the wells. Washing was performed by adding 3.6 mM $Na_2HPO_4$, 1.4 mM $KH_2PO_4$, 145 mMNaCl, and 0.05% (Vol./Vol.) Tween 20 (hereinafter, abbreviated as "PBS-T") to the wells of the microtiter plate at 200 μL/well and removing PBS-T by decantation. The washing step was performed a total of three times. After that, an HRP-labeled antibody 2 solution was added at 100 μL/well. The plate was left to stand still at 37° C. for 1 hour, and the HRP-labeled antibody 2 solution was then removed by decantation. Washing was performed by adding PBS-T at 200 μL/well and removing PBS-T by decantation. The washing step was performed a total of three times. After that, a TMB One-Step Substrate System (Dako) was used as a substrate solution for an HRP enzymatic reaction and added at 100 μL/well, and the plate was left to stand still under a light-shielding condition at 25° C. for 30 minutes. After that, a 313 mM $H_2SO_4$ solution was added at 100 μL/well as a reaction terminating solution, and each of the wells was measured for its absorbances at wavelengths of 450 nm and 630 nm using Multiskan Ascent and Ascent Software for Multiskan (Dainippon Pharmaceutical Co., Ltd.). Then, a value obtained by subtracting the absorbance at a wavelength of 630 nm from the absorbance at a wavelength of 450 nm was defined as a measured value. Native human podocalyxin extracted from the kidney was used as a standard for a calibration curve to derive a podocalyxin concentration in a specimen.

A urinary podocalyxin excretion rate as a urinary podocalyxin concentration corrected with a urinary creatinine concentration was calculated with the following equation.

Urinary podocalyxin excretion rate (μg/g)=100×urinary podocalyxin concentration (ng/mL)÷urinary creatinine concentration (mg/dL)   <Equation>

Example 2

Clinical Significance of Urinary Podocalyxin Concentration and Urinary Podocalyxin Excretion Rate in Acute Kidney Injury Urinary podocalyxin concentrations were determined for 10 patients with acute kidney injury by the method of Example 1 and compared to those of 66 healthy subjects. Table 1 below shows a pathological background which led to acute kidney injury for each of the 10 patients with acute kidney injury.

TABLE 1

| Patient | Pathological background |
|---|---|
| A-23 | Hemorrhagic shock |
| A-21 | Sigmoid colon perforation, Sepsis |
| A-20 | Hospitalization due to pneumonia |
| A-5 | Hospitalization due to airway burn |
| A-32 | Traffic injury, hemorrhagic shock |
| A-10 | Colonic diverticular perforation, Peritonitis |
| A-42 | Unknown |
| A-45 | Unknown |
| A-18 | Sepsis |
| A-46 | Unknown |

Further, in the same manner, urinary podocalyxin excretion rates were also compared between the 10 patients with acute kidney injury and the 66 healthy subjects.

FIG. 1 shows the results regarding the urinary podocalyxin concentrations. It was found that the patients with acute kidney injury had higher values for the urinary podocalyxin concentrations than the healthy subjects ($P<0.05$). When a value for the upper limit of the 95% confidence interval of the urinary podocalyxin concentrations determined for urine obtained from the healthy subjects was adopted as a reference value, the reference value was 334 ng/mL and 40% of the patients with acute kidney injury exhibited values higher than the reference value.

Figure 2:
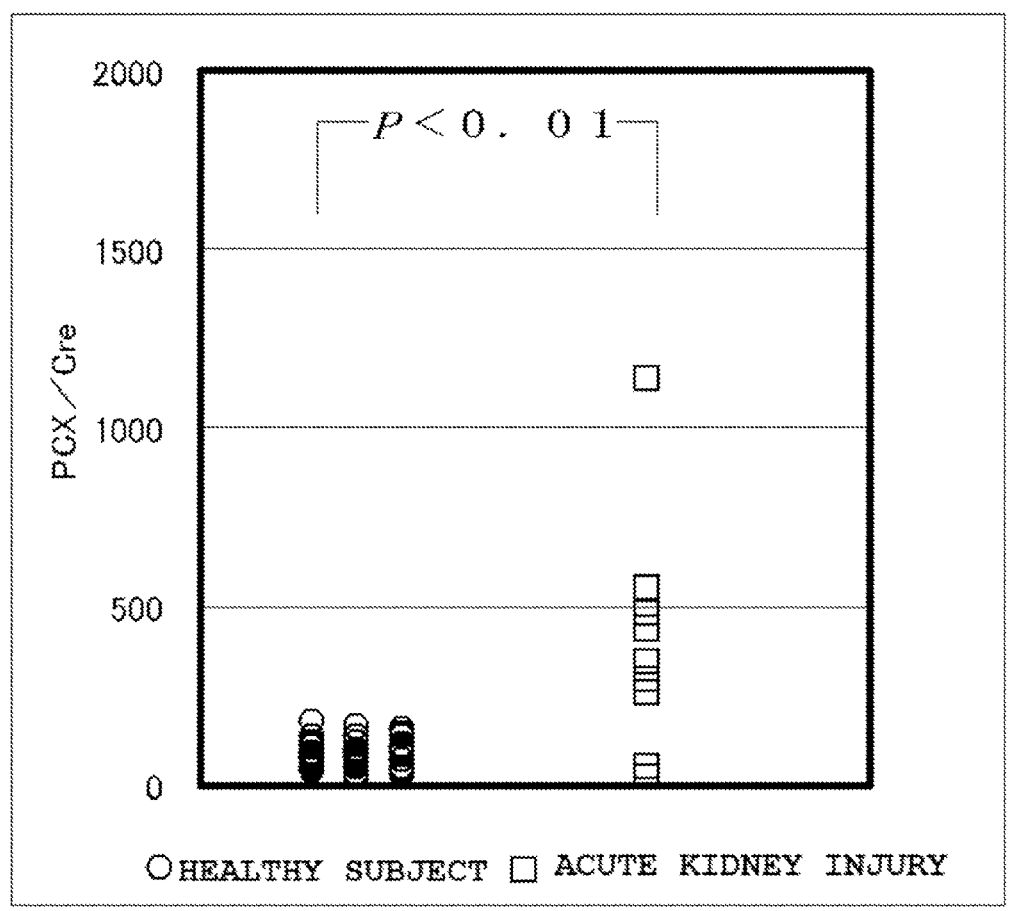
[FIG. 2] A graph showing a comparison of urinary podocalyxin excretion rates between healthy subjects and patients with acute kidney injury (Example 2).

FIG. 2 shows the results regarding the urinary podocalyxin excretion rates. It was found that the patients with acute kidney injury had higher values for the urinary podocalyxin excretion rates than the healthy subjects ($P<0.01$). When a value for the upper limit of the 95% confidence interval of the urinary podocalyxin excretion rates "PCX/Cre" determined for urine obtained from the healthy subjects was adopted as a reference value, the reference value was 161 μg/g and 80% of the patients with acute kidney injury exhibited values higher than the reference value.

INDUSTRIAL APPLICABILITY

As described above, the test method of the present invention allows acute kidney injury to be assessed accurately and quickly. The test method of the present invention uses urine as a sample, and hence, unlike a conventional method, a test can be performed non-invasively, which allows a physical burden on a patient to be reduced. Thus, the test method is useful.

The invention claimed is:

1. A test method for determining acute kidney injury in a subject, said method comprising:
   adding a treatment liquid to a urine sample of a subject to produce a urine sample solution comprising a solubilized podocalyxin;
   detecting the level of solubilized podocalyxin in said urine sample solution; and
   correlating the level of solubilized podocalyxin with the presence of acute kidney injury in said subject.

2. A test method according to claim 1, wherein said step of correlating the level of solubilized podocalyxin comprises comparing the level of solubilized podocalyxin with a reference value, and wherein said level of solubilized podocalyxin higher than said reference value is indicative of the presence of acute kidney injury.

3. A test method according to claim 2, wherein the reference value comprises a value for an upper limit of a 95% confidence interval of a value for urinary podocalyxin in a healthy subject.

4. A test method according to claim 1, wherein the value for the urinary podocalyxin comprises a value corrected with a value for a urinary component.

5. A test method according to claim 4, wherein the urinary component comprises urinary creatinine.

6. A test method according to claim 1, wherein the acute kidney injury comprises acute kidney injury due to acute tubular injury.

7. A test method according to claim 1, wherein the detecting of the urinary podocalyxin is performed by an immunological technique.

8. A test method according to claim 7, wherein a test reagent comprising an anti-podocalyxin antibody is used for detecting urinary podocalyxin.

* * * * *